United States Patent
Lee (10) Patent No.: US 8,172,994 B2
(45) Date of Patent: May 8, 2012

(54) BIOMATERIAL MEASURING DEVICE AND MANUFACTURING METHOD THEREOF

(75) Inventor: Jin-Woo Lee, Suwon-si (KR)

(73) Assignee: Ceragem Medisys Inc., Gyeonggi-Do (KR)

( * ) Notice: Subject to any disclaimer, the term of this patent is extended or adjusted under 35 U.S.C. 154(b) by 1031 days.

(21) Appl. No.: 10/582,529

(22) PCT Filed: Dec. 10, 2004

(86) PCT No.: PCT/KR2004/003237
§ 371 (c)(1),
(2), (4) Date: Nov. 25, 2008

(87) PCT Pub. No.: WO2005/057200
PCT Pub. Date: Jun. 23, 2005

(65) Prior Publication Data
US 2010/0062520 A1 Mar. 11, 2010

(30) Foreign Application Priority Data

Dec. 11, 2003 (KR) ........................ 10-2003-0090412

(51) Int. Cl.
| | |
|---|---|
| *G01N 27/26* | (2006.01) |
| *G01N 31/00* | (2006.01) |
| *G01N 33/50* | (2006.01) |
| *G01N 33/487* | (2006.01) |
| *C12Q 1/00* | (2006.01) |
| *C12M 1/34* | (2006.01) |
| *C12M 3/00* | (2006.01) |
| *H01R 43/20* | (2006.01) |

(52) U.S. Cl. ......... 204/403.03; 204/403.02; 204/403.01; 435/287.1; 29/876

(58) Field of Classification Search ............. 204/403.02, 204/403.03, 403.04, 403.14, 403.01, 403.15; 29/876
See application file for complete search history.

(56) References Cited

U.S. PATENT DOCUMENTS

| | | | |
|---|---|---|---|
| 5,120,420 | A | 6/1992 | Nankai |
| 5,395,504 | A | 3/1995 | Saurer |

(Continued)

FOREIGN PATENT DOCUMENTS

JP 62197765 9/1987

(Continued)

OTHER PUBLICATIONS

International Search Report for PCT/KR2004/003237 dated Apr. 18, 2005.

*Primary Examiner* — Jeffrey T Barton
*Assistant Examiner* — Louis Rufo
(74) *Attorney, Agent, or Firm* — Michel Morency; Foley & Lardner LLP (57) ABSTRACT

A method of producing a biomaterial measuring device is disclosed. The method includes forming a plurality of reactions elements, to which an assay reagent is applied, on a first substrate, cutting the resulting first substrate in a unit of individual reaction element, and attaching a first substrate piece, which is formed by cutting the resulting first substrate in the unit of individual reaction element, to a predetermined portion of a second substrate. In the biomaterial measuring device, since a material cost in minimized and it is easy to automate production, it is possible to reduce a production, it is possible to reduce a production cost.

10 Claims, 7 Drawing Sheets

U.S. PATENT DOCUMENTS

| | | | |
|---|---|---|---|
| 5,437,999 A | 8/1995 | Diebold | |
| 5,997,817 A | 12/1999 | Crismore | |
| 6,123,820 A * | 9/2000 | Bergkuist et al. | 204/411 |
| 6,316,283 B1 | 11/2001 | Saurer | |
| 2003/0200644 A1* | 10/2003 | Matzinger | 29/592.1 |
| 2003/0201175 A1* | 10/2003 | Musho et al. | 204/403.01 |
| 2004/0067166 A1* | 4/2004 | Karinka et al. | 422/82.03 |
| 2006/0064035 A1* | 3/2006 | Wang et al. | 600/583 |

FOREIGN PATENT DOCUMENTS

| | | |
|---|---|---|
| JP | 01308962 | 12/1989 |
| WO | WO-97/25613 | 7/1997 |
| WO | WO-01/02839 | 1/2001 |

\* cited by examiner

FIG. 1 -- PRIORT ART --

BIOMATERIAL MEASURING DEVICE AND MANUFACTURING METHOD THEREOF

TECHNICAL FIELD

The present invention relates, in general, to a biomaterial measuring device and a method of producing the same and, more particularly, to a biomaterial measuring device and a method of producing the same, in which a plurality of reaction elements is formed on a substrate, the resulting substrate is cut in a reaction element unit, and the resulting elements are attached to another substrate acting as a mechanical supporter.

BACKGROUND ART

A biosensor, in which a biomaterial is used as a tracing device and which has excellent sensitivity and reaction specificity, is expected to be applied to various fields, such as medical/pharmaceutical fields (clinical chemical assay and remedy), and process and environmental monitoring and chemical stability evaluation in the bio-industry. Particularly, a chemical composition assay in vivo is medically very important, and recently, the biosensor has been frequently used to assay a biomaterial sample containing blood in a medical diagnosis field. Of various biosensors, a biosensor, which employs an enzyme assay method using a characteristic reaction of an enzyme to a matrix or of an enzyme to an inhibitor, is most frequently used in hospitals and clinical chemical assays because ease of application is assured, measurement sensitivity is excellent, and the results are rapidly obtained. The enzyme assay method, which is applied to the biosensor, may be classified into an optical method, in which light transmittance is measured through a spectroscopic assay before and after an enzyme reaction, and an electrode method, in which an electrochemical signal is measured. Compared to the electrode method, the optical method is difficult to use assay of critical biomaterial because the measuring time is long, a great amount of blood is required, and measurement error occurs due to turbidity of a biomaterial sample. Accordingly, recently, the electrode method has been frequently applied to a biosensor using an enzyme. In the electrode method, after an electrode system is formed on a plastic film, an assay reagent is applied to an electrode, a sample is introduced, and specific components of the sample are quantitatively measured using a predetermined electric potential.

U.S. Pat. Nos. 5,120,420, 5,395,504, 5,437,999, and 5,997,817 are patent literatures of a biosensor, which disclose embodied operations and effects of the biosensor in detail. The disclosures of the above patents are incorporated herein by reference as follows.

Figure 1:
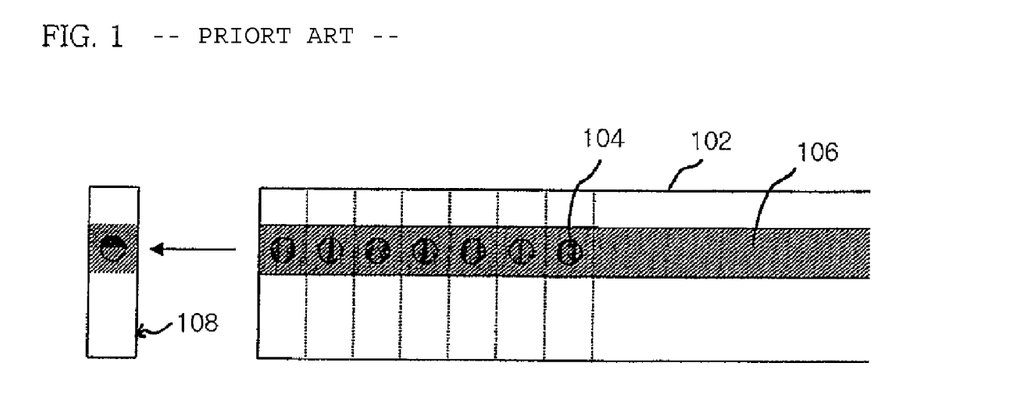
FIG. 1 illustrates the production of a strip using a conventional optical method.

FIG. 1 illustrates the production of a strip using a conventional optical method. Holes 104 are formed through a substrate 102 to allow light to penetrate therethrough, and a membrane 106, to which a biochemical reaction reagent is applied, is attached thereto. Subsequently, the resulting structure is cut into strips 108.

In the method, since the strips must be produced in a handy size, the strips are formed so as to be a few cm long. Hence, the size of a production device increases and the device costs a great deal. Since the strip is typically provided in a roll form, the substrate 102 is made of a flexible material. Accordingly, a process error occurs in the course of forming the holes by punching or of forming the strips by cutting, and thus, the uniformity of measurements is undesirably reduced. Furthermore, there is a limit that only one reaction element can be produced using one strip.

Figure 2:
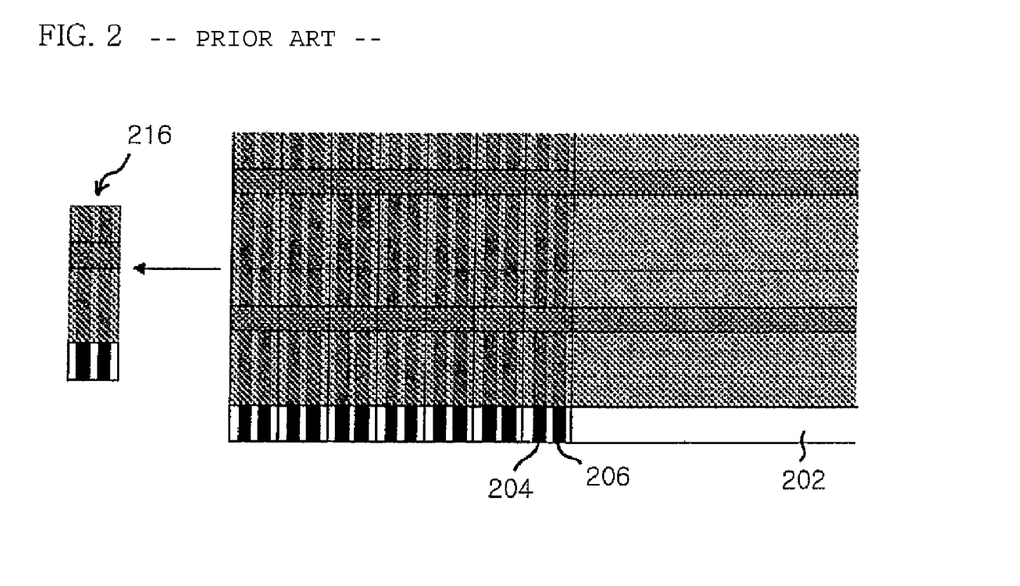
FIG. 2 illustrates the production of a biosensor strip using a conventional electrochemical method.
Figure 3:
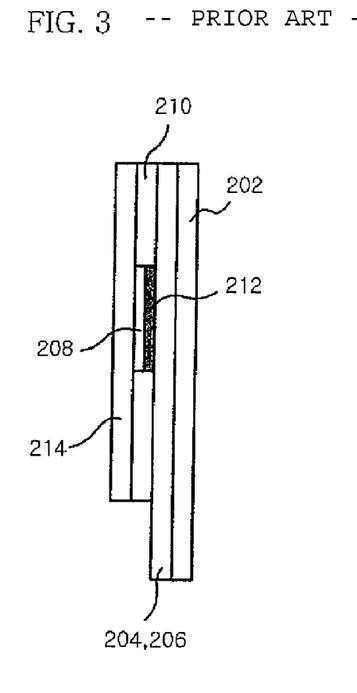
FIG. 3 is a sectional view of the biosensor strip of FIG. 2.

FIG. 2 illustrates the production of a biosensor strip using a conventional electrochemical method. FIG. 3 is a sectional view of the biosensor strip of FIG. 2. For convenience of understanding, thicknesses of layers are exaggerated in FIG. 3. After an operation electrode 204, a standard electrode 206, and an auxiliary electrode (not shown), on which a redox reaction occurs, are formed on an insulator 202, an insulator 210, which is processed in a predetermined shape to form a capillary 208 for feeding a sample therethrough and which acts as a spacer, is attached to the resulting insulator 202. Subsequently, a biochemical reagent 212 is applied to the electrodes, and an insulator 214 is attached thereto to form a cover, thereby completing the biosensor, in which the biochemical reagent 212 is contained in the capillary 208, through the electrochemical method. Finally, the resulting structure is cut into strips 216.

As in the production of the strips using the conventional optical method, the strips must be produced in a handy size, thus the strips are formed so as to be a few cm long. Since the electrodes must be formed on every strip, it is difficult to implement the production in a roll form, and thus, the production is typically carried out in a sheet form. When the production is conducted in the sheet manner, it is necessary to carefully handle the entire surface of a sheet because each strip is large. To produce the strips having uniform performance using a wide sheet, it is necessary to take a care in the formation of the electrodes. Additionally, since application of a solution must be conducted throughout the wide area, it is difficult to assure uniformity during a drying process. Therefore, a production device is large and costly, it is difficult to implement the production, and the production cost is high. The insulator 202 is made of a relatively thin plastic material so as to be cut into strips. When using glass or silicon wafer, the material cost of the substrate increases per strip, thus the price of the strip increases. As well, there is a limit that only one reaction element can be produced using one strip. Furthermore, a capillary having one structure can be formed in one process. If capillaries having two structures are formed, the production cost doubles.

DISCLOSURE OF THE INVENTION

Accordingly, the present invention has been made keeping in mind the above problems occurring in the prior art, and an object of the present invention is to provide a biomaterial measuring device and a method of producing the same, in which a material cost is minimized and it is easy to automate the production, thereby reducing a production cost.

Another object of the present invention is to provide a biomaterial measuring device and a method of producing the same, in which it is possible to attach a plurality of reaction elements to one substrate, thereby reducing a price per reaction element.

A further object of the present invention is to provide a biomaterial measuring device, in which, since a substrate is made of plastic, silicone, or glass, according to the type of reactant and a characteristic of a reaction, process compatibility is improved, and which can be applied to the expanded range of biochemical assay, and a method of producing the same.

Yet another object of the present invention is to provide a biomaterial measuring device, in which, since a plurality of reaction elements for measuring the same object material (or assay material) is attached to one substrate, or a plurality of reaction elements for measuring different object materials is attached to the one substrate, various applications are possible, usability is maximized, and sequential measurement is possible, and a method of producing the same.

Still another object of the present invention is to provide a biomaterial measuring device, which is packaged in a magazine manner, thus reducing inconvenience when a user must exchange it every measurement, and a method of producing the same.

Still another object of the present invention is to provide a biomaterial measuring device, in which the amount of sample needed during measurement is minimized, and a method of producing the same.

In order to accomplish the above objects, the present invention provides a method of producing a biomaterial measuring device. The method comprises forming a plurality of reaction elements, to which an assay reagent is applied, on a first substrate, cutting the resulting first substrate into individual reaction elements, and attaching a first substrate piece, which is formed by cutting the resulting first substrate into individual reaction elements, to a predetermined portion of a second substrate. The method may further comprise mounting a dehumidifying agent for removing moisture, which is fed from the environment to the assay reagent, on a predetermined portion of the biomaterial measuring device while the dehumidifying agent is isolated from the environment.

Preferably, a plurality of first substrate pieces, which are formed by cutting the resulting first substrate into individual reaction elements, is attached to the second substrate. The second substrate is made of any one selected from the group consisting of plastic, glass, and semiconductor wafer.

When the biomaterial measuring device employs an optical assay, light may penetrate through the portion of the second substrate, to which the first substrate piece is attached. The assay reagent may be layered on a membrane so as to be applied to the first substrate, or be directly applied to the first substrate. Furthermore, means may be additionally formed on the portion of the second substrate, to which the first substrate piece is attached, to focus or defocus light.

When the biomaterial measuring device employs an electrochemical assay, the formation of the plurality of reaction elements comprises forming at least two first electrodes on a first side of the first substrate, and applying the assay reagent through the first electrodes. The method may further comprise forming a second electrode on a second side of the first substrate, which is opposite to the first side, and electrically connecting at least one of the first electrodes on the first side to the second electrode on the second side. The first electrodes on the first side may be electrically connected to the second electrode on the second side through a via hole which is formed through the first substrate, a wall of which is coated with a conductor.

Additionally, the present invention provides another method of producing the biomaterial measuring device. The method comprises forming a plurality of first reaction elements, to which a first assay reagent is applied, on a first substrate, forming a plurality of second reaction elements, to which a second assay reagent is applied, on a second substrate, cutting the first and second substrates into individual reaction elements, and attaching first and second substrate pieces, which are formed by cutting the first and second substrates into individual reaction elements, to predetermined portions of a third substrate.

As well, the present invention provides a biomaterial measuring device. The device comprises a first substrate, an assay reagent, which is applied on an entire first side of the first substrate to form a reaction element, and a second substrate, on which the first substrate is mounted to enable the assay reagent to form a path for feeding a biomaterial therethrough.

In a biomaterial measuring device according to the present invention, since a material cost is minimized and it is easy to automate production, it is possible to reduce a production cost. Further, it is possible to attach a plurality of reaction elements to one substrate, thereby reducing the price per reaction element. Furthermore, since the substrate is made of plastic, silicone, or glass according to the type of reactant and a characteristic of a reaction, process compatibility is improved, and the device can be applied to an expanded range of biochemical assays. Additionally, since a plurality of reaction elements for measuring the same object material is attached to one substrate, or a plurality of reaction elements for measuring different object materials is attached to one substrate, various applications are possible, usability is maximized, and sequential measurement is possible. As well, the biomaterial measuring device is packaged in a magazine manner, thus reducing inconvenience when a user must exchange a strip every measurement. Furthermore, if using an optical method, it is possible to install a lens to focus light, thus reducing a reaction area, thereby minimizing the amount of sample needed during measurement. This has very important significance when blood-gathering is repeatedly conducted for a regular medical examination. Additionally, if using an electrochemical method, since; it is possible to freely control the shape of a capillary, the amount of sample needed during measurement is reduced.

BEST MODE FOR CARRYING OUT THE INVENTION

Hereinafter, a detailed description will be given of embodiments of the present invention with reference to the drawings. In the drawings, the same reference numerals are used throughout the different drawings to designate the same or similar components.

Figure 4:
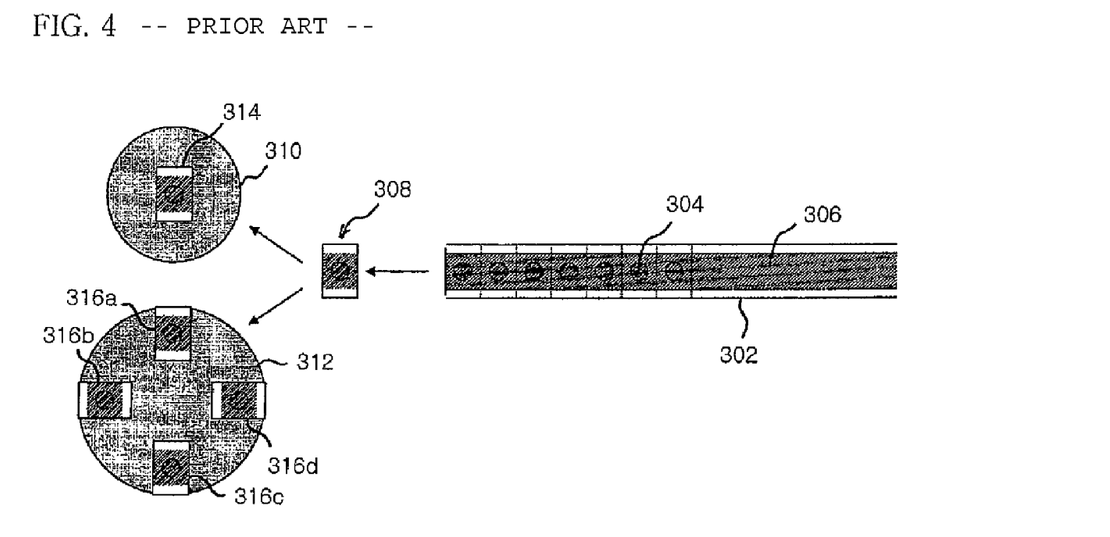
FIG. 4 illustrates the production of a chip using an optical method according to the present invention.

FIG. 4 illustrates the production of a chip using an optical method according to the present invention. The procedure of producing a reaction element is the same as a conventional procedure. In other words, holes 304 are formed through a substrate 302 to allow light to penetrate therethrough, and a membrane 306, to which a biochemical reagent is applied, is attached thereto. Subsequently, the resulting structure is cut into reaction elements 308.

Next, the cut reaction elements 308 are attached to separate attachment substrates 310, 312. If holes are already formed through the substrates 310, 312, it is possible to attach the reaction elements 308 to the attachment substrates 310, 312 while the membrane 306 is not attached to the substrate 302. In this case, the preparation of the substrate 302 and the formation of the holes through the substrate 302 may be omitted. In the present invention, the biochemical reagent is applied to the substrate 302 after it is layered on the membrane 306. However, it may be directly applied to the substrate 302 without being layered on the membrane 306.

The attachment substrates 310, 312 may be made of any one selected from rigid plastic, glass, or silicon wafer. In consideration of processability, it is preferable to use a plastic substrate, such as a polycarbonate, used as the material for a compact disk. Since the plastic substrate may be produced through an injection molding process, a process error of the hole is insignificant, and the plastic substrate may be processed into various shapes, such as a circle, triangle, or square, and thus, it is applied to various fields. If the attachment substrates 310, 312 are made of glass or silicon wafer, it is possible to form a structure using anisotropic etching or isotropic etching.

If using the attachment substrate 310, the attachment of the reaction element 308 to the attachment substrate is implemented in such a way that only the one reaction element 314 is attached to the attachment substrate. On the other hand, if using the attachment substrate 312, since it is possible to attach two or more reaction elements 316a, 316b, 316c, 316d to the attachment substrate, the production cost per reaction element is reduced. When the attachment of the four reaction elements is conducted, the four reaction elements for measuring the same object may be attached, or alternatively, the four reaction elements for measuring different objects may be attached. For example, the four reaction elements for measuring glucose may be attached, or alternatively, the reaction elements for measuring different objects of glucose, cholesterol, HDL, and LDL may be attached to the attachment substrate 312 to produce a chip. If the objects, which must be clinically measured together, such as glucose, glycated hemoglobin (HbAlc), and hemoglobin (Hb), are analyzed, availability is improved and it is possible to produce goods having high added value.

Figure 5:
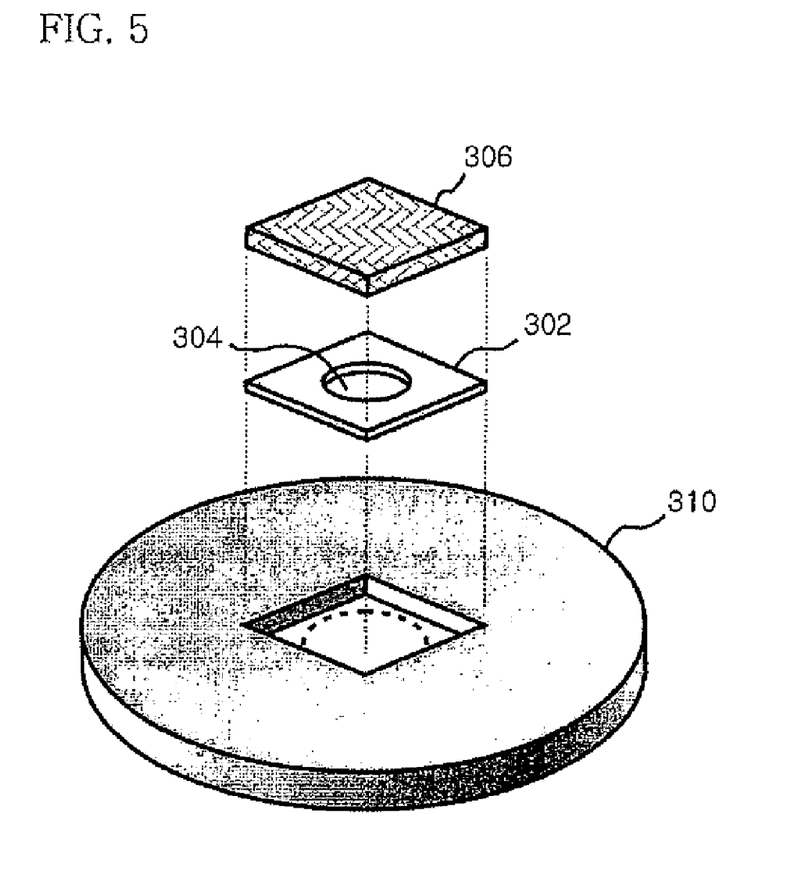
FIG. 5 illustrates the chip using the optical method according to an embodiment of the present invention.
Figure 6:
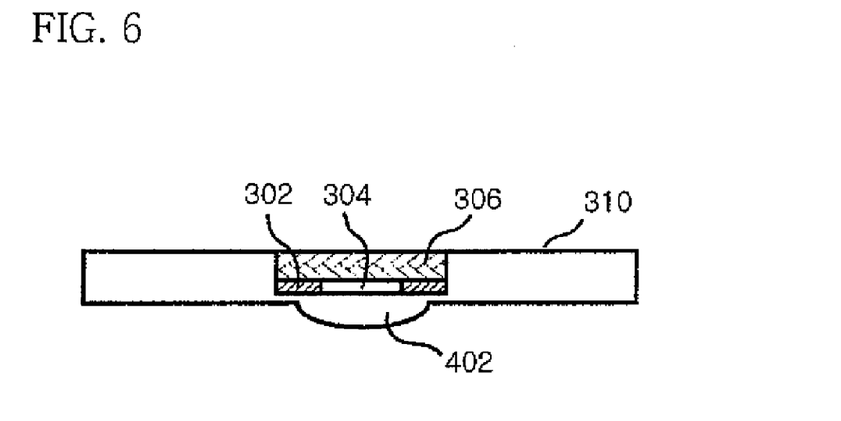
FIG. 6 is a sectional view of the chip of FIG. 5.

FIG. 5 illustrates a chip using an optical method according to the present invention, and FIG. 6 is a sectional view of the chip of FIG. 5. In FIGS. 5 and 6, reference numerals 302, 304, 306, 310, and 402 denote a substrate, a hole, a membrane to which a biochemical reagent is applied, an attachment substrate, and a lens integrated with the attachment substrate 310, respectively. Since light is focused using the lens 402, it is possible to reduce a reaction area so as to minimize the amount of sample needed during measurement.

Figure 7:
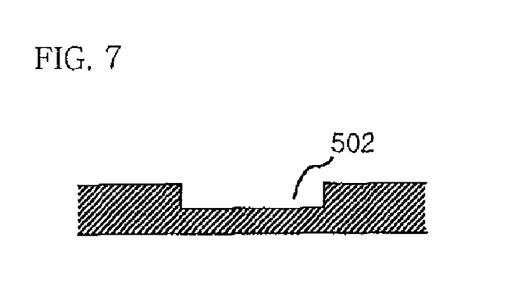
FIGS. 7 to 13 are sectional views of various attachment substrates of chips using the optical method according to the present invention.
Figure 8:
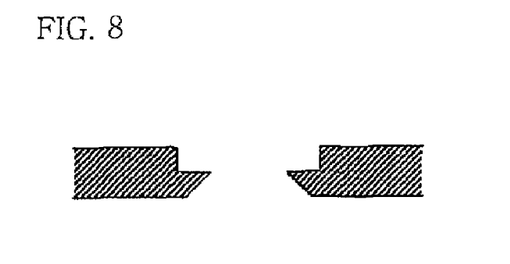
Figure 9:
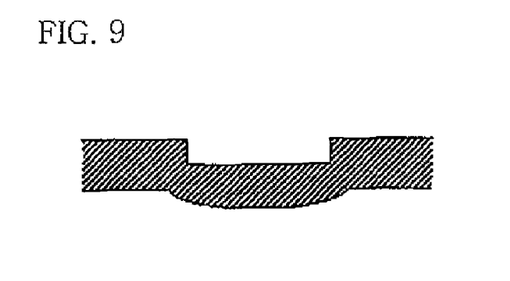
Figure 10:
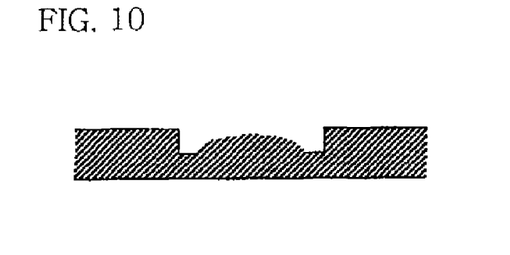
Figure 11:
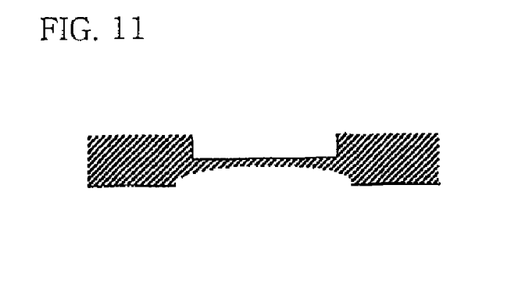
Figure 12:
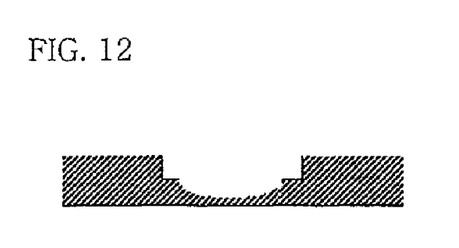
Figure 13:
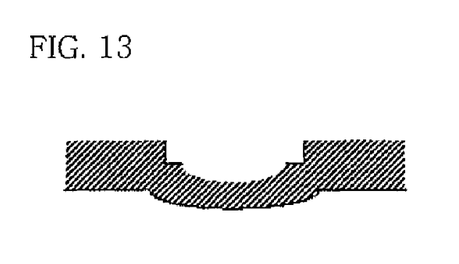

FIGS. 5 to 13 are sectional views of various attachment substrates of the chips using the optical method according to the present invention. As described above, when the attachment substrates 310, 312 are produced through an injection molding process using plastic as a material, it is possible to produce them in a predetermined shape. FIG. 7 illustrates an attachment substrate, which is not processed, except that a groove 502 for receiving the reaction element 308 is formed on the substrate. FIG. 8 illustrates an attachment substrate through which a hole is already formed. In this case, it is unnecessary to use a transparent material, but it is preferable to use a black or opaque material which does not reflect light. In particular, it is possible to use reused plastic, contributing to the reduction of environmental pollution. FIGS. 9 and 10 illustrate an attachment substrate on which a convex lens is formed, FIGS. 11 and 12 illustrate an attachment substrate on which a concave lens is formed, and FIG. 13 illustrates an attachment substrate on which convex and concave lenses are formed simultaneously.

Figure 14:
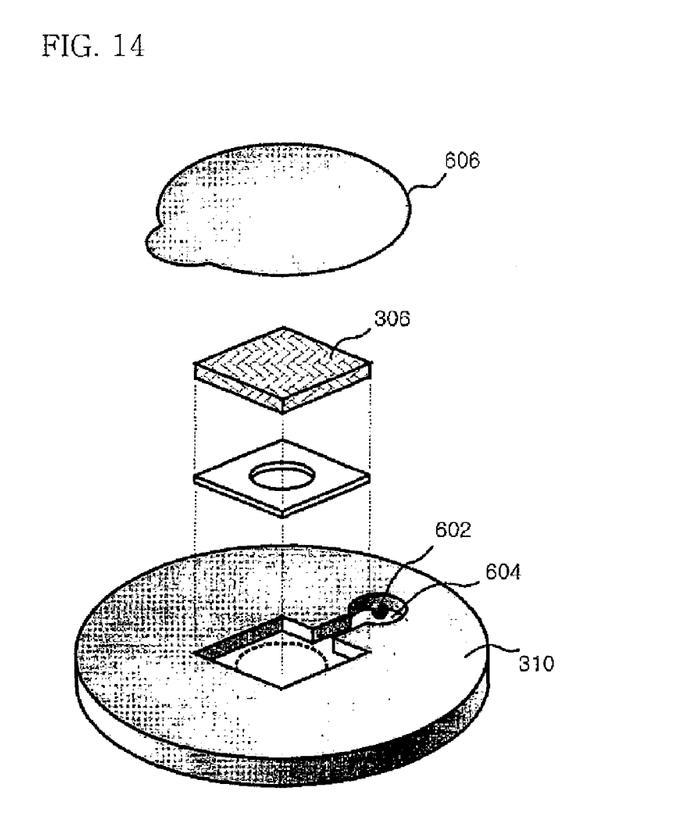
FIG. 14 illustrates a chip using an optical method according to another embodiment of the present invention.

Meanwhile, since the attachment substrate is thicker than a conventional strip-type plastic film and it is possible to produce the attachment substrate through an injection molding process, various functions may be additionally provided. FIG. 14 illustrates a chip using an optical method, on which a dehumidifying agent is mounted. It is very important for a biochemical reagent to be dehumidified so as to assure stability for a long time. As shown in FIG. 14, a space 604 for storing a dehumidifying agent 602 is formed on the attachment substrate 310. A cover 606, which forms the top of the resulting attachment substrate, is provided so as to isolate the space 604 for the dehumidifying agent and a membrane 306, to which a biochemical reagent is applied, from the environment. The dehumidifying agent 602 may be produced in a predetermined shape, such as circular or granular shape, and thus, it is preferable to form the space 604 for the dehumidifying agent so as to correspond in shape to the dehumidifying agent 602. Other components are the same as those of FIG. 4.

Figure 15:
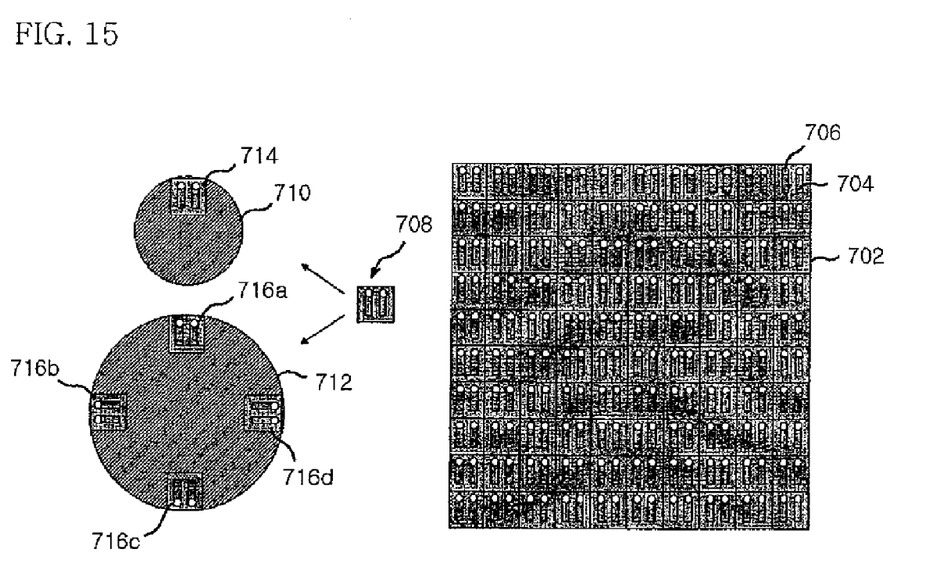
FIG. 15 illustrates the production of a biosensor chip using an electrochemical method according to the present invention.

FIG. 15 illustrates the production of a biosensor chip using an electrochemical method according to the present invention. As shown in FIG. 15, after an electrode 704 and a via hole 706 are formed on an insulator 702, a biochemical reagent (not shown) is applied on the resulting insulator through a dot dispensing process or a spin coating process. The resulting structure is cut into reaction elements 708, and they are attached to separate attachment substrates 710, 712 on which capillaries are already formed. The via hole 706 electrically connects the electrode 704, formed on an upper side of the insulator 702, to an electrode (not shown) formed on a lower side, that is, an opposite side of the upper side. A conductor is applied on a wall of the via hole. In the specification, the via hole is used as a comprehensive notion, and includes a conductive rod.

The insulator 702 may be made of any one selected from rigid plastic, glass, or silicon wafer. In consideration of processability, it is preferable to use a plastic substrate, such as polycarbonate, used as a material for compact disks, or to use a printed circuit board (PCB). Particularly, when employing the PCB frequently used in the industrial world, the formation of the via hole 706 is very easily conducted because it is possible to automatically form the via hole using existing facilities.

A portion of the electrode 704 on the upper side of the insulator 702, to which the biochemical reagent is applied, may be made of a predetermined electrode material. Any material, which is used as an electrode material in electrochemistry, may be used, and the electrode material may be exemplified by carbon, carbon paste (carbon containing Au, Ag, or the like), Ag/AgCl, gold, platinum, and palladium. The electrode (not shown), which is formed on the lower side of the insulator 702, transfers an electric signal, which is formed by a reaction between the biochemical reagent and an object, to a measuring device. Hence, the electrode may be made of a wiring material, such as copper having excellent electric conductivity, which is typically used in the PCB because it has no connection with a biochemical reaction.

The attachment substrates 710, 712 may be made of any one selected from rigid plastic, glass, or silicon wafer. In consideration of processability, it is preferable to use a plastic substrate, such as polycarbonate, used as a material for compact disks, or to use a PCB. Particularly, since the plastic substrate may be produced through an injection molding process, it is possible to form a capillary through one process and to process the capillary in various shapes. Furthermore, since a plurality of capillaries having different shapes is formed on one attachment substrate, it is possible to analyze the different objects using one attachment substrate. As well, the attachment substrate may be formed in various shapes, such as a circle, triangle, or square, and thus, it may be applied to various fields.

If using the attachment substrate 710, the attachment of the reaction element 708 to the attachment substrate is implemented in such a way that only one reaction element 714 is attached to the attachment substrate. On the other hand, if using the attachment substrate 712, since it is possible to attach two or more reaction elements 716a, 716b, 716c, 716d to the attachment substrate, the production cost per reaction element is reduced. When four reaction elements are attached, four reaction elements for measuring the same object may be attached, or alternatively, four reaction elements for measuring different objects may be attached. For example, four reaction elements for measuring glucose may be attached, or alternatively, reaction elements for measuring different objects, such as glucose, cholesterol, HDL, and LDL may be attached to the attachment substrate 312 to produce a chip. If the objects, which must be clinically measured together, such as glucose, glycated hemoglobin (HbA1c), and hemoglobin (Hb), are analyzed, availability is improved and it is possible to produce goods having high added value.

In the biosensor chip using the conventional electrochemical method as shown in FIG. 2, a reaction between the object and the biochemical reagent mostly occurs in the reaction element, which includes the capillary, in practice, and the performance of a product depends on the application of the biochemical reagent to the electrode therein. The remaining portion of the electrode serves only to transfer an electric signal, and thus, it need not be carefully produced. Accordingly, in the present invention, after the reaction elements are precisely produced, they are attached to a substrate which is capable of transferring an electric signal therethrough. This is the core characteristic of the present invention.

In a process of forming the electrode, the electrode must be formed in an area of an A4-sized paper (210 mm×297 mm) in order to produce two hundred conventional biosensors having a size of 7.5 mm×35 mm. On the other hand, in the present invention, the electrode is formed in an area (100 mm×100 mm) that is smaller than half a sheet of A4-sized paper. Therefore, since an operation area, required by a screen printer and a sputter used to produce the electrode, is reduced, device expenses are reduced and it is possible to gain high uniformity. As well, application of a solution is easily implemented, and uniformity of application of the reagent is improved because an area to be dried after the application is reduced. Furthermore, it is possible to employ a spin coating process instead of a dot dispensing process, thus improving productivity.

Figure 16:
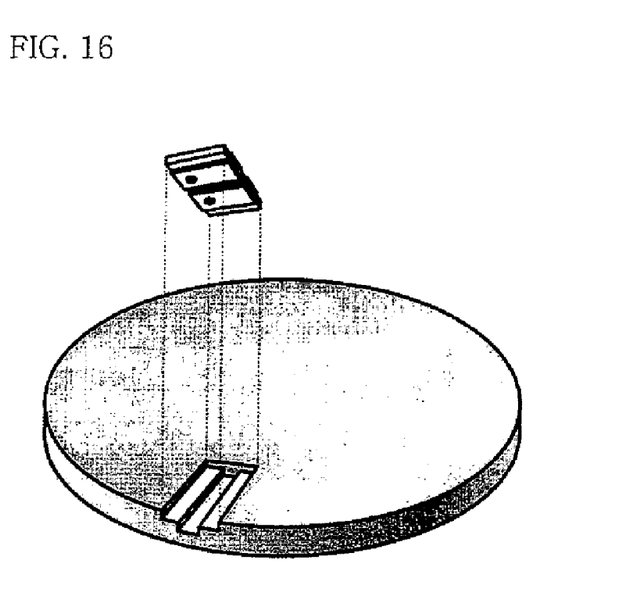
FIG. 16 illustrates a biosensor chip using an electrochemical method according to an embodiment of the present invention.
Figure 17:
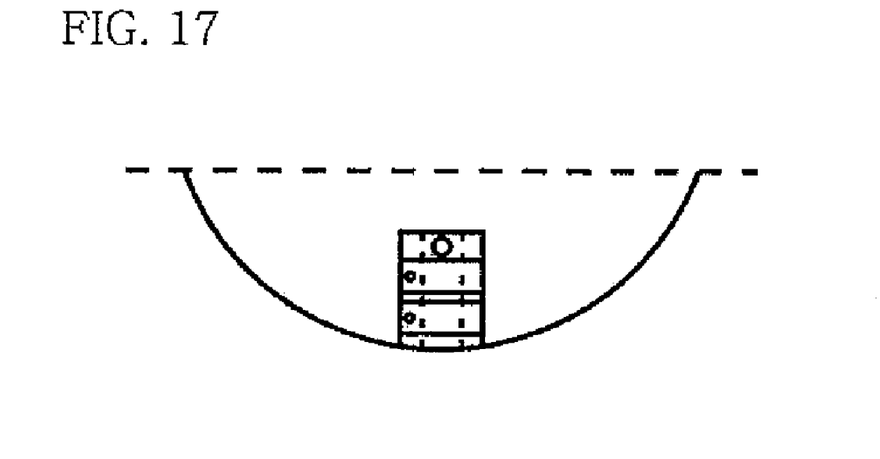
FIG. 17 is a partial sectional view of the biosensor chip of FIG. 16.
Figure 18:
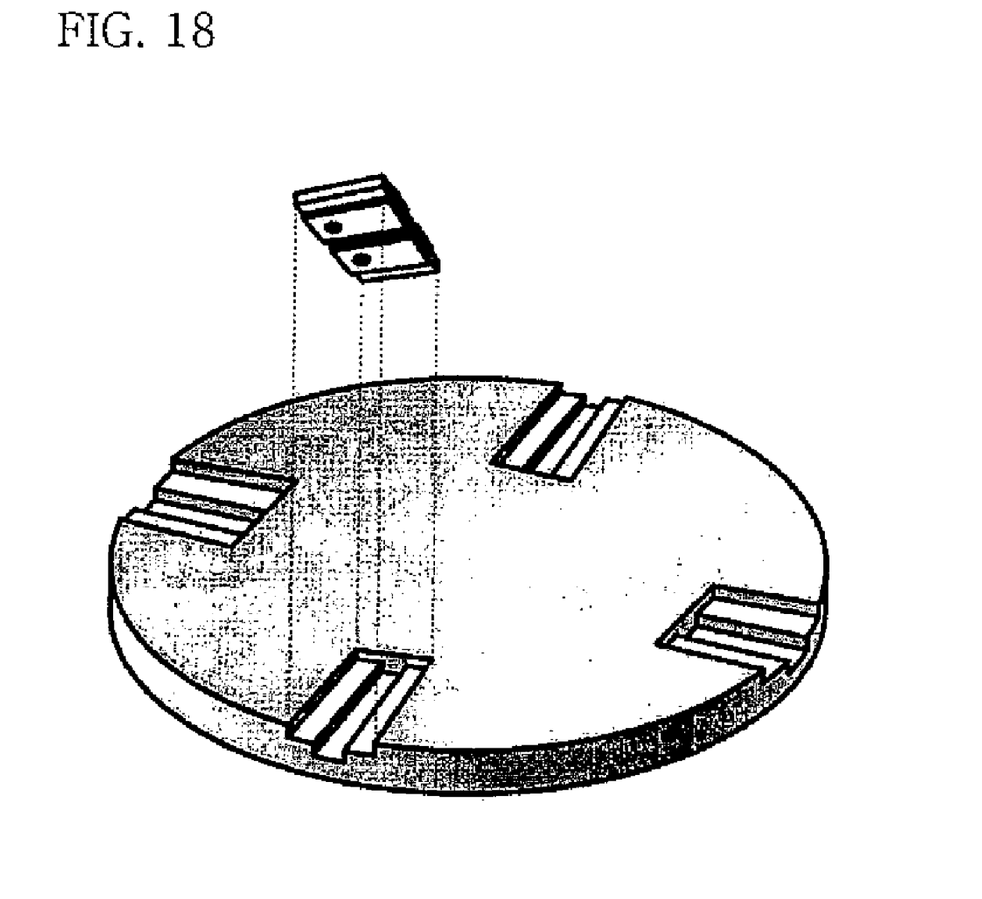
FIG. 18 illustrates a biosensor chip using an electrochemical method according to another embodiment of the present invention.

FIG. 16 illustrates a biosensor chip using an electrochemical method according to an embodiment of the present invention, and FIG. 17 is a partial sectional view of the biosensor chip of FIG. 16. FIG. 16 shows the attachment of one reaction element to an attachment substrate. FIG. 18 illustrates a biosensor chip using an electrochemical method according to another embodiment of the present invention, in which a plurality of reaction elements is attached to one attachment substrate. Constitutions of the above biosensor chips are shown in FIG. 15.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

INDUSTRIAL APPLICABILITY

As described above, in a biomaterial measuring device according to the present invention, since a material cost is minimized and it is easy to automatize production, it is possible to reduce a production cost. Further, it is possible to attach a plurality of reaction elements to one substrate, thereby reducing the price per reaction element. Furthermore, since the substrate is made of plastic, silicone, or glass according to the type of reactant and a characteristic of a reaction, process compatibility is improved, and the device can be applied to an expanded range of biochemical assays. Additionally, since a plurality of reaction elements for measuring the same object material is attached to one substrate, or a plurality of reaction elements for measuring different object materials is attached to one substrate, various applications are possible, usability is maximized, and sequential measurement is possible. As well, the biomaterial measuring device is packaged in a magazine manner, thus reducing inconvenience when a user must exchange a strip every measurement. Furthermore, if using an optical method, it is possible to install a lens to focus light, thus reducing a reaction area, thereby minimizing the amount of sample needed during measurement. This has very important significance when blood-gathering is repeatedly conducted for a regular medical examination. Additionally, if using an electrochemical method, since it is possible to freely control a capillary shape, the amount of sample needed during measurement is reduced.

The invention claimed is:

1. A method of producing a biomaterial measuring device that uses an electrochemical assay, comprising:
   forming a plurality of reaction elements on a first substrate, wherein forming a reaction element comprises:
   forming at least two first electrodes on a first side of the first substrate,
   forming a second electrode on a second side of the first substrate, wherein the second electrode transmits an electrical signal to a measuring device,
   forming a via hole through the first substrate,
   electrically connecting, through the via hole, the first electrodes on the first side of the first substrate to the second electrode on the second side of the first substrate, and
   applying an assay reagent to the first electrodes on the first side of the first substrate;
   cutting the first substrate into a plurality of reaction elements;
   forming at least one cavity, each with space for a capillary, on one side of a second substrate; and
   forming at least one capillary, by attaching the first side of at least one reaction element into at least one of the cavities in the second substrate, wherein each capillary is for feeding a biomaterial therethrough.

2. The method as set forth in claim 1, wherein the plurality of reaction elements are attached to the second substrate.

3. The method as set forth in claim 1, further comprising mounting a dehumidifying agent for removing moisture, which is introduced from an environment to the assay reagent, on a predetermined portion of the biomaterial measuring device while the dehumidifying agent is isolated from the environment.

4. A biomaterial measuring device that uses an electrochemical assay, comprising:
   a first reaction element comprising:
      a first substrate,
      a plurality of first electrodes on a first side of the first substrate,
      a second electrode on a second side of the first substrate,
      a via hole through the first substrate for electrically connecting the electrodes on the first side of the first substrate to the second electrode on the second side of the first substrate,
      an assay reagent applied to the first electrodes; and
   a second substrate having at least one cavity, each with space for a capillary, on one side of the second substrate, wherein the first side of the reaction element is mounted into one of the at least one cavities in the second substrate, and
   a capillary, formed by mounting of the reaction element one of the at least one cavities in the second substrate,
   wherein the assay reagent reacts with a biomaterial introduced through the capillary to generate an electrical signal, and
   wherein the generated electrical signal is transmitted to a measuring device through the second electrode.

5. The biomaterial measuring device as set forth in claim 4, wherein the second substrate is made of any one selected from the group consisting of plastic, glass, and semiconductor wafer.

6. The biomaterial measuring device as set forth in claim 4, further comprising a second reaction element, wherein the second reaction element comprises:
   a first substrate,
   a plurality of first electrodes on a first side of the first substrate,
   a second electrode on a second side of the first substrate,
   a via hole through the first substrate for electrically connecting the electrodes on the first side of the first substrate to the second electrode on the second side of the first substrate, and
   an assay reagent applied to the first electrodes,
   wherein the second reaction element substrate is mounted into one of the at least one cavities in the second substrate.

7. The biomaterial measuring device as set forth in claim 4, wherein the first substrate is formed of an insulating material.

8. The biomaterial measuring device as set forth in claim 4, wherein the second electrode on the second side of the first substrate is formed of an electrical conductive material.

9. The biomaterial measuring device as set forth in claim 4, further comprising a dehumidifying agent which is mounted on a predetermined portion of the biomaterial measuring device so that the dehumidifying agent is isolated from an environment and which removes moisture introduced from the environment to the assay reagent.

10. The biomaterial measuring device as set forth in claim 7, wherein the insulating material is one of a printed circuit board, a plastic substrate, a glass substrate, and a semiconductor wafer.

* * * * *